US012239759B2

(12) United States Patent
Perrin et al.

(10) Patent No.: US 12,239,759 B2
(45) Date of Patent: *Mar. 4, 2025

(54) SURGICAL ADHESIVES

(71) Applicants: COHESIVES, Dijon (FR); UNIVERSITE DE PAU ET DU PAYS DE L'ADOUR, Pau (FR); UNIVERSITE DE BORDEAUX, Bordeaux (FR); INSTITUT POLYTECHNIQUE DE BORDEAUX, Talence (FR); CENTRE NATIONAL DE LA RECHERCHE SCIENTIFIQUE, Paris (FR)

(72) Inventors: Bertrand Perrin, Dijon (FR); Christophe Derail, Cescau (FR); Laetitia Badie, Ibos (FR); Eric Papon, Saint Magne de Castillon (FR)

(73) Assignees: COHESIVES, Dijon (FR); UNIVERSITE DE PAU ET DU PAYS DE L'ADOUR, Pau (FR); UNIVERSITE DE BORDEAUX, Bordeaux (FR); INSTITUT POLYTECHNIQUE DE BORDEAUX, Talence (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 87 days.

This patent is subject to a terminal disclaimer.

(21) Appl. No.: 17/562,381

(22) Filed: Dec. 27, 2021

(65) Prior Publication Data

US 2022/0143264 A1     May 12, 2022

Related U.S. Application Data

(63) Continuation of application No. 15/575,678, filed as application No. PCT/FR2016/051211 on May 20, 2016, now Pat. No. 11,207,443.

(30) Foreign Application Priority Data

May 21, 2015   (FR) ...................................... 1554583

(51) Int. Cl.
| A61L 24/06 | (2006.01) |
| A61B 17/00 | (2006.01) |
| A61L 24/00 | (2006.01) |

(52) U.S. Cl.
CPC ........ *A61L 24/06* (2013.01); *A61B 17/00491* (2013.01); *A61L 24/001* (2013.01); *A61B 2017/005* (2013.01)

(58) Field of Classification Search
CPC . A61L 24/06; A61L 24/001; A61B 17/00491; A61B 2017/005
See application file for complete search history.

(56) References Cited

U.S. PATENT DOCUMENTS

| 2005/0032952 A1* | 2/2005 | Bonfanti ................ C09J 167/00 524/492 |
| 2007/0134333 A1 | 6/2007 | Thomas et al. |
| 2010/0104349 A1* | 4/2010 | Broadley ......... A61B 17/00491 401/193 |
| 2010/0152880 A1* | 6/2010 | Boyden ................ A61K 9/1617 700/283 |
| 2014/0194887 A1 | 7/2014 | Shenoy |
| 2016/0121018 A1 | 5/2016 | Watanabe et al. |

FOREIGN PATENT DOCUMENTS

| EP | 1994886 A1 | 11/2008 |
| WO | 2012088059 A2 | 6/2012 |

OTHER PUBLICATIONS

Badie et al., "Photo-polymerized adhesives for biological tissues", Radtech Conference 2015 (4 pages).
International Search Report dated Aug. 24, 2016 from corresponding International Application No. PCT/FR2016/051211 (6 pages).
PCT (Written Opinion) dated May 20, 2016 from corresponding International Application No. PCT/FR2016/051211 ( 5 pages).
Ahmed., "Hydrogel: Preparation, characterization, and applications: a review", Journal of Advanced Research, 2015; 17 pages.

* cited by examiner

*Primary Examiner* — Thomas McEvoy
(74) *Attorney, Agent, or Firm* — Maier & Maier, PLLC

(57) ABSTRACT

A composition for the adhesion of biological tissues to one another, for the adhesion of a material to a biological tissue, for the adhesion of an adhesive or of a substance to the surface of a biological tissue, for blocking an orifice in a biological tissue, for reinforcing a biological tissue and/or for fixing and stabilising a biological tissue. A monomer that is polymerisable under the effect of ultraviolet (UV) radiation and in that the viscosity of said composition is less than 10 mPa·s at 20° C.

27 Claims, No Drawings

SURGICAL ADHESIVES

TECHNICAL FIELD

The present invention relates to the field of surgical adhesives, more specifically the present invention relates to compositions intended to be used in a method for the adhesion of biological tissues to one another, for the adhesion of a material to a biological tissue, for the adhesion of an adhesive or of a substance to the surface of a biological tissue, for blocking an orifice (haemostasis, aerostasis) in a biological tissue, for reinforcing a biological tissue and/or for fixing and stabilising a biological tissue.

BACKGROUND

Prior Art

A certain number of surgical techniques implement surgical adhesives. The latter are mainly used to help obtain a surgical haemostasis. However, the effectiveness of surgical adhesives in this specification is contentious and other uses, like for aerostasis do not show better results.

Moreover, surgical adhesives have very weak adhesive properties and cannot therefore be used as an adhesive nor as a surgical suture. The application of surgical adhesives is done most of the time directly on the tissue, without preparing the adhesive surface. Penetration into tissues is weak or non-existent, which leads to a low-quality adhesive. The filing parties have observed that current adhesives do not bond and do not penetrate into tissues. Consequently, they have developed an adhesive able to deeply penetrate into the surface of the biological tissue in order to achieve an integration of the adhesive in the tissue.

For example, it is known from document EP1994886A1, a surgical adhesive comprising polymerisable monomers of the cyanoacrylate family. The polymerisation of the latter is triggered by the humidity of the biological tissue as soon as contact is made between the surgical adhesive and the biological tissue. Consequently, despite the low viscosity of this surgical adhesive, the polymerisation of the cyanoacrylate monomers occurs on the surface of the biological tissue. Thus, the cyanoacrylate monomers cannot penetrate into the biological tissue. Cyanoacrylate monomers cannot be integrated into the tissue, which explains the low mechanical resistance and low clinical effectiveness of cyanoacrylate-based surgical adhesives.

Thus, the present invention proposes to supply a new type of surgical adhesives. The compositions and the method according to the invention enable to obtain an effective and resistant adhesion. The rupture of the adhesion is made by the propagation of a fracture in the bonded tissue or in the adhesive seal and not in the adhesive/tissue interface. Adhesion is applicable to any type of biological tissues (soft tissues, bone tissues). Such an adhesion moreover enables to obtain an effective haemostasis or an effective aerostasis. It also enables the surgical suture to be replaced with an adhesion.

SUMMARY OF THE INVENTION

The principle of the invention consists of letting a polymerisable monomer penetrate into the biological tissue, which reinforces the adhesion properties of the surface of the tissue.

Thus, the present invention relates to a composition intended to be used in a method for the adhesion of biological tissues to each other, for the adhesion of a material to a biological tissue, for the adhesion of an adhesive or a substance to the surface of a biological tissue, for blocking an orifice (haemostasis, aerostasis) in a biological tissue, for reinforcing a biological tissue and/or for fixing and stabilising a biological tissue, notable in that it comprises a polymerisable monomer under the effect of ultraviolet (UV) radiation and in that its viscosity is less than 10 mPa·s at 20° C.

The present invention also relates to a composition for a use in a method for the adhesion of biological tissues to each other, for the adhesion of a material to a biological tissue, for the adhesion of an adhesive or a substance to the surface of a biological tissue, for blocking an orifice (haemostasis, aerostasis) in a biological tissue, for reinforcing a biological tissue and/or for fixing and stabilising a biological tissue, notable in that it comprises a polymerisable monomer under the effect of ultraviolet (UV) radiation and in that its viscosity is less than 10 mPa·s at 20° C.

The viscosity of the composition can, in particular, be measured by a falling sphere viscometer according to the standard DIN53015.

Indeed, the filing parties have been able to highlight that the viscosity of said composition enabled to obtain a significant penetration into biological tissues and an optimal adhesion.

In the framework of the present invention, the term "polymerisable monomer" means a monomer of which the polymerisation can be initiated under the effect of ultraviolet (UV) radiation. This method of initiation of the polymerisation enables to expect that the composition of monomers had penetrated into the tissues before triggering the polymerisation. Preferably, the polymerisation of the composition according to the invention can only be initiated by ultraviolet radiation and excluding any other method of initiation. In particular, the initiation of the polymerisation of the polymerisable monomers consists of irradiation by UV rays. Preferably, said UV ray has a wavelength of between 150 nm and 280 nm, even more preferably between 170 nm and 260 nm, and absolutely preferably between 190 nm and 240 nm.

According to another preferred embodiment, said UV ray has a wavelength of between 200 nm and 400 nm, even more preferably between 300 nm and 400 nm, and absolutely preferably between 350 nm and 400 nm.

The polymer obtained after polymerisation of the monomer is preferably a biocompatible polymer.

For these reasons, the composition according to the invention does not comprise polymerisable monomers of which the polymerisation can be initiated just by the contact of water molecules. Thus, instant polymerisation of the composition according to the invention on tissue contact is avoided.

For these same reasons, the composition according to the invention does not comprise polymerisable monomers of the cyanoacrylate family known for quickly polymerising on contact with water and/or surrounding humidity.

Preferably, the polymerisable monomer is only polymerisable by irradiation by UV rays.

According to a preferred embodiment, said viscosity is less than 6 mPa·s at 20° C. According to an even more preferred embodiment, said viscosity is less than 4 mPa·s at 20° C.

According to an absolutely preferred embodiment, said viscosity is less than 2 mPa·s at 20° C. and more specifically between 1 and 2 mPa·s at 20° C.

According to a preferred embodiment, the composition according to the invention is not a hydrogel.

According to a preferred embodiment, said monomer is a methacrylate acrylate monomer or an acrylate oligomer or methacrylate oligomer.

According to a preferred embodiment, said monomer comprises a polar function.

In the framework of the present invention, the term "polar function" makes reference to a group of atoms wherein the electrons are distributed asymmetrically, thus enabling this polar function to participate in electrostatic interactions. Said polar function can, in particular, be chosen in the group comprising hydroxyl, amide, carboxyl, amino, carbonate, carbamate, sulphonamide, sulphonic, phosphonic, methoxyethyl, methoxyethoxyethyl, hydroxyethyl and hydroxyethoxyethyl functions.

According to a preferred embodiment, said acrylate monomer is chosen in the group comprising the mono-, di-, tri-, tetra- and penta-acrylate or methacrylate, and their mixtures.

According to a preferred embodiment, said acrylate monomer is chosen in the group comprising acrylic acid, methyl methacrylate; dimethylaminoethyl methacrylate; ethyl acrylate; cyclohexyl methacrylate; 2-hydroxyethyl methacrylate; 3-hydroxypropyl acrylate; alpha-bromoethyl acrylate; alpha-chloroethyl acrylate; chloromethyl methacrylate; 2-bromoethyl methacrylate; 2-naphtyl methacrylate; paratolyl acrylate; parachlorophenyl methacrylate; metabromophenyl acrylate; 2,4,6-tribromophenyl acrylate; paracholorobenzyl methacrylate; metamethoxybenzyl methacrylate; paraethylbenzyl acrylate; 1,6-hexanediol dimethacrylate; neopentylglycol diacrylate; thiodiethylene-glycol dimethacrylate; bisphenol A ethoxyl diacrylate; bisphenol A ethoxyl dimethacrylate; pentaerythritol triacrylate; glyceryl triacrylate; dipentaerythritol pentaacrylate; trimethylolpropane triacrylate; tris isocyanurate trimethacrylate (2-hydroxyethyl); trimethylolpropane polyoxyethylene triacrylate; a urethane acrylate; a urethane methacrylate; bis sulphur (4-methacryloylthiophenyl); tert-butyl acrylate; an ethyleneglycol or a polyethyleneglycol chosen in the group composed of acrylate, methacrylate; diacrylate, dimethacrylate and their mixtures.

According to an absolutely preferred embodiment, said acrylate monomer is chosen in the group, hydroxy(ethyl) methacrylate, acrylic acid, hydroxy(propyl)methacrylate, tert-butyl acrylate, dimethylaminoethyl methacrylate and their mixtures.

According to an absolutely preferred embodiment, said acrylate monomer is chosen in the group comprising acrylic acid, (hydroxyethyl)methacrylate, (hydroxypropyl)methacrylate and their mixtures.

According to another absolutely preferred embodiment, said acrylate monomer is chosen in the group comprising acrylic acid, tert-butyl acrylate and their mixtures.

According to another absolutely preferred embodiment, said acrylate monomer is chosen in the group comprising acrylic acid, dimethylaminoethyl methacrylate and their mixtures.

According to a preferred embodiment, said monomer has a molar mass of between 50 and 300 g·mol$^{-1}$.

According to a preferred embodiment, said monomer has a concentration of between 90% and 100% in mass in relation to the total mass of the composition.

According to a preferred embodiment, said composition further comprises a cross-linking agent.

According to a preferred embodiment, said composition only comprises said monomer or said monomer and a cross-linking agent.

A person skilled in the art is able to choose the most suitable cross-linking agent according to the monomer used.

According to a preferred embodiment, said cross-linking agent comprises an acrylate function.

According to a preferred embodiment, said cross-linking agent is chosen in the group comprising multifunctional acrylates in particular comprising 1,6-hexanediol diacrylate, trimethylolpropane triacrylate, 1,2-ethylene glycol diacrylate, pentaerythritol tetracrylate and mixtures of these.

According to another preferred embodiment, said cross-linking agent is chosen in the group comprising multifunctional acrylates comprising in particular hexanediol dimethylacrylate (HDDMA), ethylene glycol dimethylacrylate (EGDMA), butanediol diacrylate (BDDA), poly(ethylene glycol) diacrylate (PEGDA) and mixtures of these.

According to a preferred embodiment, said cross-linking agent is present at a concentration of between 1% and 5% in mass, still more preferably between 1% and 3% in mass, still more preferably between 1% and 2% in mass in relation to the total mass of the composition.

According to a preferred embodiment, said cross-linking agent is present at a concentration of between 0.1% and 3% in mass, still more preferably between 0.1% and 0.5% in mass, still more preferably between 0.1% and 0.3% in mass and absolutely preferably at a concentration of 0.2% in mass in relation to the total mass of the composition.

According to a preferred embodiment, the composition according to the invention comprises a photoinitiator. A person skilled in the art will choose the most suitable photoinitiator according to the emission spectrum of the lamp used.

The photoinitiator can be chosen from among: 2.2-dimethoxyphenyl-2-acetophenone (DMPA), camphorquinone or 4.4'-bis(diethylamino)benzophenone, this list being non-exhaustive.

Advantageously, the photoinitiator is used at a concentration of between 0.2% and 1%, preferably between 0.2% and 0.3% in mass.

According to a preferred embodiment, said photoinitiator is DMPA.

According to an embodiment of the invention, said composition comprises a solvent and still more preferably said solvent is water. According to another preferred embodiment, said solvent is an alcohol and absolutely preferably, ethanol.

According to another preferred embodiment, said composition has no solvent.

In the framework of the present invention, the term "comprises" means that the composition according to the invention includes the cited elements. Preferably, the present invention relates to compositions only comprising the elements cited excluding any other.

The present invention also relates to a method for the adhesion of biological tissues to one another, for the adhesion of a material to a biological tissue, for the adhesion of an adhesive or a substance to the surface of a biological tissue, for blocking an orifice (haemostasis, aerostasis) in a biological tissue, for reinforcing a biological tissue and/or for fixing and stabilising a biological tissue, notable in that it comprises the steps:
  (i) coating the tissue to treat with a composition according to the invention,
  (ii) letting the composition penetrate into said tissue, (iii) inducing, by UV radiation, the polymerisation of said composition.

The method according to the invention is advantageously non-invasive. The term "non-invasive" means that the method according to the invention comprises no surgical step consisting of accessing the tissue to be treated. Thus, the method according to the invention is implemented on a directly accessible biological tissue (e.g. the skin) or previously made accessible by other methods.

The characteristics of the UV ray implemented, in particular its power and its wavelength, are adapted to the components of the composition, in particular to the type of the polymerisable monomer and to its concentration in the composition.

According to a preferred embodiment, said method further comprises after step (iii), a step (iv) consisting of the apposition of a synthetic tissue to the surface of the tissue.

According to a preferred embodiment, said UV ray has a wavelength of between 150 nm and 280 nm.

According to a preferred embodiment, said UV ray has a power of between 100 W and 200 W.

The present invention also relates to a kit of parts comprising a composition according to the invention and a UV radiation source. Preferably, the UV radiation source of the kit of parts can emit a UV ray adapted to polymerise and/or assist with the polymerisation and/or accelerate the polymerisation of the polymerisable monomer of the composition.

In the framework of the present invention, the term "UV radiation source" makes reference to any artificial means able to produce a UV ray and more specifically, a ray with a wavelength of between 150 nm and 280 nm, still more preferably, between 170 nm and 260 nm and absolutely preferably between 190 nm and 240 nm. Preferably, said UV ray has a power of between 0.5 W and 200 W and absolutely preferably, of between 100 W and 200 W.

According to another preferred embodiment, the term "UV radiation source" makes reference to any artificial means able to produce a UV ray with a wavelength of between 200 nm and 400 nm, still more preferably, between 300 nm and 400 nm and absolutely preferably between 350 nm and 400 nm.

Preferably, said UV ray has a wavelength of between 150 nm and 280 nm and of a power of between 100 W and 200 W.

Acrylic acid, (hydroxyethyl)methacrylate/acrylic acid, (hydroxypropyl)methacrylate/acrylic acid, acrylic acid/tert-butyl acrylate/cross-linking agent, methacrylate/acrylic acid/(hydroxyethyl)methacrylate/cross-linking agent solutions, or acrylic acid/dimethylaminoethyl methacrylate/cross-linking agent solutions of variable viscosity and concentrations have been deposited in samples of bovine pericardium. This step is carried out at 20° C. Said pericardium samples have been subjected to 150 W UV radiation, for a duration of 5 minutes, in order to trigger the polymerisation of the monomers. The radiation source has been positioned 10 cm away from the pericardium.

Said pericardium samples have then been covered with a strip of glassfibre, the latter has then received a monomer solution identical to that used in the preceding step.

The pericardium samples have been subjected to UV radiation under the identical conditions as those in the preceding step.

A peeling test has then been carried out by traction at 180° C. on the glassfibre strip in a furnace regulated at 37° C. The rest time for the strip installed between the jaws of the traction machine is one minute, the temperature within the sample is, at the time of starting the test, 30° C., + or −4° C.

An acrylic acid solution has been deposited on the pericardium samples. Said pericardium samples have been subjected to UV radiation of 150 W, for 5 minutes, in order to trigger the polymerisation of the monomers. The radiation source has been positioned 10 cm away from the pericardium.

The pericardium samples have then been transversally cut and observed by scanning electronic microscopy.

The results obtained are presented in the table below.

In all the tests carried out, it has been observed, whatever the adhesive used, a rate of around 70% rupture in the tissue or the glassfibre strip and 30% in the adhesive. When the rupture occurs in the adhesive, the force necessary to destroy the assembly is equal to the force obtained for a rupture in the glassfibre.

It has been observed that the resistance to rupture (that is, the resistance to the bonding), increases inversely to the viscosity, of the composition according to the invention, used.

TABLE 1

| Composition used (all compositions comprise 0.25% in DMPA mass) | Viscosity [mPa · s] | Resistance to rupture F/b [N/m] in the pericardium |
|---|---|---|
| 100% acrylic acid | 1 | 300 |
| 25% HEMA 75% AA | 3 | 300 |
| 50% HEMA 50% AA | 4 | 250 |
| 75% HEMA 25% AA | 6 | 200 |
| 25% HPMA 75% AA | 3 | 400 |
| 50% HPMA 50% AA | 4.5 | 300 |
| 75% HPMA 25% AA | 6.5 | 100 |
| 65% AA 35% tBuAC 2% HDDMA | 1.23 | 400 |
| 50% AA 50% tBuAC 2% HDDMA | 1.23 | 190 |
| 50% AA 25% HEMA 25% MA 2% HDDMA | 1.81 | 190 |
| 90% AA 10% DMAEMA 2% HDDMA | 9.6 | 322 |
| 65% AA 35% tBuAC 2% EGDMA | 1.18 | 343 |
| 65% AA 35% tBuAC 2% BDDA | 1.27 | 286 |
| 65% AA 35% tBuAC 2% PEGDA | 1.5 | 382 |

The presence of the formed polymer has been observed, penetrated into the surface of the tissue over a depth of 50 μm. Moreover, it has been observed that the formed polymer has penetrated into the spaces between the tissues' collagen fibres.

This observation indicates the capacity of the compositions according to the invention to penetrate into tissues which explains the perfect adhesion obtained.

The invention claimed is:

1. A composition, intended to be used in a method for adhesion of biological tissues to one another, for adhesion of a material to a biological tissue, for adhesion of an adhesive or of a substance to a surface of the biological tissue, for blocking an orifice in the biological tissue, for reinforcing the biological tissue and/or for fixing and stabilizing the biological tissue, comprising:
   a cross-linking agent comprising an acrylate function;
   a monomer polymerizable under the effect of ultra-violet (UV) radiation, wherein a viscosity of the composition is less than 10 mPa·s at 20° C., and wherein the composition is not a hydrogel.

2. The composition according to claim 1, wherein said UV radiation has a wavelength of between 150 nm and 280 nm.

3. The composition according to claim 1, wherein the polymerization of the monomer is only initiated by irradiation by the UV radiation.

4. The composition according to claim 1, wherein the composition does not comprise polymerizable monomers of which polymerization can be initiated by contact with water molecules.

5. The composition according to claim 1, wherein the composition does not comprise polymerizable monomers of the cyanoacrylate family.

6. The composition according to claim 1, wherein the viscosity of the composition is less than 6 mPa·s at 20° C.

7. The composition according to claim 1, wherein the viscosity of the composition is less than 2 mPa·s at 20° C.

8. The composition according to claim 1, wherein said monomer is an acrylate monomer or a methacrylate monomer or an acrylate oligomer or a methacrylate oligomer.

9. The composition according to claim 1, wherein said monomer comprises a polar function.

10. The composition according to claim 9, wherein said polar function is chosen in the group comprising hydroxyl, amide, carboxyl, amino, carbonate, carbamate, sulfonamide, sulfonic, phosphonic, methoxyethyl, methoxyethoxyethyl, hydroxyethyl and hydroxyethoxyethyl functions.

11. The composition according to claim 9, wherein said monomer is chosen in the group comprising the mono-, di-, tri-, tetra- and penta-acrylate or methacrylate, and their mixtures.

12. The composition according to claim 8, wherein said acrylate monomer is chosen in the group comprising acrylic acid, methyl methacrylate; dimethylaminoethyl methacrylate; ethyl acrylate; cyclohexyl methacrylate; 2-hydroxyethyl methacrylate; 3-hydroxypropyl acrylate; alpha-bromoethyl acrylate; alpha-chloroethyl acrylate; chloromethyl methacrylate; 2-bromoethyl methacrylate; 2-naphtyl methacrylate; paratolyl acrylate; parachlorophenyl methacrylate; metabromophenyl acrylate; 2,4,6-tribromophenyl acrylate; paracholorobenzyl methacrylate; metamethoxybenzyl methacrylate; paraethylbenzyl acrylate; 1,6-hexanediol dimethacrylate; neopentylglycol diacrylate; thiodiethylene-glycol dimethacrylate; bisphenol A ethoxyl diacrylate; bisphenol A ethoxyl dimethacrylate; pentaerythritol triacrylate; glyceryl triacrylate; dipentaerythritol pentaacrylate; trimethylolpropane triacrylate; tris isocyanurate trimethacrylate (2-hydroxyethyl); trimethylolpropane polyoxyethylene triacrylate; a urethane acrylate; a urethane methacrylate; bis sulfur sulphur (4-methacryloylthiophenyl); tert-butyl acrylate; an ethyleneglycol or a polyethyleneglycol chosen in the group composed of acrylate, methacryleglycol; diacrylate, dimethacrylate and their mixtures.

13. The composition according to claim 8, wherein said acrylate monomer is chosen in the group comprising hydroxy (ethyl) methacrylate, acrylic acid, hydroxy (propyl) methacrylate, tert-butyl acrylate, dimethylaminoethyl methacrylate and their mixtures.

14. The composition according to claim 1, wherein said monomer has a molar mass of between 50 and 300 g·mol-1.

15. The composition according to claim 1, wherein the composition has no solvent.

16. The composition according to claim 1, wherein said monomer has a concentration of between 90 and 100% in mass in relation to a total mass of the composition.

17. The composition according to claim 1, wherein said cross-linking agent is chosen in the group comprising multifunctional acrylates comprising in particular 1,6-hexanediol dimethylacrylate (HDDMA), ethylene glycol dimethylacrylate (EGDMA), butanediol diacrylate (BDDA), trimethylolpropane triacrylate, 1,2-ethylene glycol diacrylate, poly(ethylene glycol)diacrylate (PEGDA), pentaerythritol tetracrylate and mixtures of these.

18. The composition according to claim 1, wherein said cross-linking agent is present at a concentration of between 1% and 5% in mass.

19. The composition according to claim 1, further comprising a photoinitiator.

20. The composition according to claim 19, wherein said photoinitiator is chosen in the group comprising 2,2-dimethoxyphenyl-2-acetophenone (DMPA), camphorquinone and 4.4'-bis(diethylamino)benzophenone.

21. The composition according to claim 19, wherein said photoinitiator is at a concentration of between 0.2% and 1%.

22. A non-invasive method for adhesion of a biological tissues to one another, for adhesion of a material to a biological tissue, for adhesion of an adhesive or a substance to a surface of the biological tissue, for blocking an orifice in the biological tissue, for reinforcing the biological tissue and/or for fixing and stabilizing the biological tissue, comprising:
(i) coating the tissue to treat with the composition according to claim 1,
(ii) letting the composition penetrate into said biological tissue, and
(iii) inducing, by UV radiation, polymerization of said composition.

23. The method according to 22, further comprising:
(iv) bringing a synthetic tissue into apposition to the surface of said biological tissue.

24. The method according to claim 22, wherein said UV radiation has a wavelength of between 150 nm and 280 nm.

25. The method according to claim 22, wherein said UV radiation has a power of between 100 W and 200 W.

26. A kit of parts comprising the composition according to claim 1 and a UV radiation source.

27. A composition, intended to be used in a method for adhesion of biological tissues to one another, for adhesion of a material to a biological tissue, for adhesion of an adhesive or of a substance to a surface of a biological tissue, for blocking an orifice in a biological tissue, for reinforcing a biological tissue and/or for fixing and stabilizing a biological tissue, comprising:
a photoinitiator, wherein the photoinitiator is chosen in the group comprising 2,2-dimethoxyphenyl-2-acetophenone (DMPA), camphorquinone and 4.4'-bis(diethylamino)benzophenone;
a monomer polymerizable under the effect of ultra-violet (UV) radiation, wherein a viscosity of the composition is less than 10 mPa·s at 20° C., and wherein the composition is not a hydrogel.

* * * * *